United States Patent [19]

Marshall

[11] Patent Number: 4,793,285
[45] Date of Patent: Dec. 27, 1988

[54] AUTOMATIC MILKING APPARATUS AND METHODS

[75] Inventor: Barry R. Marshall, Ramsden, England

[73] Assignee: Ambic Equipment Limited, Oxfordshire, England

[21] Appl. No.: 928,547

[22] Filed: Nov. 10, 1986

[30] Foreign Application Priority Data

Nov. 12, 1985 [GB] United Kingdom ............... 8527864

[51] Int. Cl.⁴ .............................................. A01J 7/00
[52] U.S. Cl. .............................. 119/14.02; 119/14.14; 119/14.55
[58] Field of Search ............... 119/14.14, 14.15, 14.17, 119/14.54, 14.55, 14.02

[56] References Cited

U.S. PATENT DOCUMENTS

| | | | |
|---|---|---|---|
| 2,329,396 | 9/1943 | Dinesen | 119/14.55 X |
| 3,022,766 | 2/1962 | McKinley | 119/14.14 |
| 4,395,972 | 8/1983 | Griffin | 119/14.55 |
| 4,403,568 | 9/1983 | Fukuhara et al. | 119/14.54 |
| 4,574,736 | 3/1986 | Tanaka et al. | 119/14.14 X |

Primary Examiner—Robert P. Swiatek
Attorney, Agent, or Firm—Larson and Taylor

[57] ABSTRACT

A method of automatic milking permitting continuous electrical monitoring of milk-related values, such as milk conductivity and milk temperature, for detecting diseased cows. The method uses a claw-piece with four short-milk tubes and teat cups, as is customary, but mixing of milk from different cow's quarters is prevented by valves within the claw-piece base. Within the base, the four channels from the four input nipples each contains milk from one cow's quarter solely. Groups of electrical sensors extend into each of the four channels for monitoring the milk-related values. The method relates in particular to hydraulic milking, when no air-bleed is provided upstream of the claw-piece. Suitable apparatus is described for carrying out the method.

7 Claims, 2 Drawing Sheets

AUTOMATIC MILKING APPARATUS AND METHODS

DESCRIPTION OF THE INVENTION

This invention relates to automatic milking apparatus and methods.

The object of the invention is to provide a method of automatic milking whereby the milking process can be monitored by electrical means throughout the milking process and to provide apparatus suitable for this purpose.

BACKGROUND OF THE INVENTION

In any milking herd, the detection of mastitis at an early stage, in any beast, is of the utmost importance.

It has for many years been known that the electrical conductivity of the milk taken from a cow gives an indication of the presence of mastitis, in that the electrical conductivity increases with increasing extent of infection. Electrical conductivity measuring cells for milking apparatus have been proposed, yet none is in common use at the present time. The usual method of detecting mastitis is by the detection of milk clots in milk passing through the milk line of individual cows being milked.

Commonly-used automatic milking apparatus uses a claw-piece having connections, by four short-milk tubes, to the four teat cups, for milking the four quarters of an individual cow. Connections to the claw-piece are provided from a pulsating vacuum source and a connection from the claw-piece is provided to the milk flow line. A continuous air-bleed is provided into the milk line on the upstream side of the claw-piece.

Recent study of the operation of such milking apparatus has disclosed that, in operation, milk from any one short-milk tube passes into the other three, so that the milk in any short-milk tube at any given time is not solely drawn from one quarter.

Mastitis, when it appears in a beast, normally appears first in one quarter, from which it may spread to the other quarters of the same beast and to other beasts of the herd. Consequently, early detection of mastitis means detection of mastitis in a single quarter. Yet, in present-day milking apparatus, there is no point in the system where solely milk from one quarter may be monitored.

This is believed, by the present inventor, to be one reason why monitoring by electrical conductivity has not been reliable nor found widespread use.

A further reason for unreliability of the method is the presence of air in the milk stream due to the air-bleed upstream of the claw-piece.

A second monitoring value of concern is the temperature of milk drawn from a cow, since this may give indication of sickness of a beast. However, again such measurement is rendered unreliable in present-day milking apparatus due, for example, to the introduction of cold air into the warm milk by reason of the continuous air-bleed.

A further monitoring value of importance is the volume, or weight, of milk drawn from each beast milked. It would be of value to know the quantity of milk drawn from each quarter and electrical flow-metering devices which might be fitted in the short-milk path are known. Yet with reverse-flow and the mixing of milk in the short-milk tubes, such measurement is not effective. Presently, milk volume is measured by recorder jars located in the long milk tube from each claw-piece.

Recently, however, there has been developed, and described in British patent specification No. 2,057,845, a claw-piece with integral valves, one at the connection of each short-milk tube. This claw-piece prevents the mixing of milk from one short-milk tube into another. Furthermore, it appears that this type of claw-piece is likely to come into widespread use for milking. Such an arrangement, preventing the mixing of milk from different quarters, is considered to be an essential feature of the present invention.

More recently, also, there has been developed, and described in British patent specification No. 8,512,941, a method of automatic milking, using such a valve claw-piece, wherein the introduction of air into the milk flow upstream of the valves is not permitted. This method is known as hydraulic milking and is regarded as a preferred feature of the present invention.

The object of this invention, therefore, is to provide monitor means for milking systems using the recent advances in milking technology mentioned above.

Accordingly, the present invention provides automatic milking apparatus comprising a claw-piece, a cluster of four short-milk tubes and associated teat cups for milking a cow's four quarters, a one-way valve system associated with the four short-milk tubes effective to prevent milk from one cow's quarter entering the short-milk tube of another quarter, a group of electrodes or electrical sensors associated with each of the four short-milk tubes, for continuously taking electrical measurement of a plurality of values relating to the milk passing through the related short-milk tube, switch means for selecting electrodes or sensors of the four groups for monitoring, a data processing unit for converting electrical signals in the various electrode or sensor circuits into meaningful values and display means for the visual display of such values.

Preferably, the said claw-piece and cluster operate without the introduction of air into the milk flow upstream of the valve system.

According to another aspect, the present invention provides a method of automatic milking of a cow's four quarters using a claw-piece and cluster of four short-milk tubes and teat cups, ensuring by valve means that milk from any one quarter does not enter the short-milk tube of another quarter, monitoring by electrical means a plurality of milk-related values for the milk flowing from all four quarters, selecting the values and quarter's milk to be monitored at any one time and providing a visual display of the values so monitored.

SHORT DESCRIPTION OF THE DRAWINGS

One embodiment of the invention will now be described in detail, by way of example, with reference to the accompanying drawings, in which.

DESCRIPTION OF THE EMBODIMENT

Figure 1:
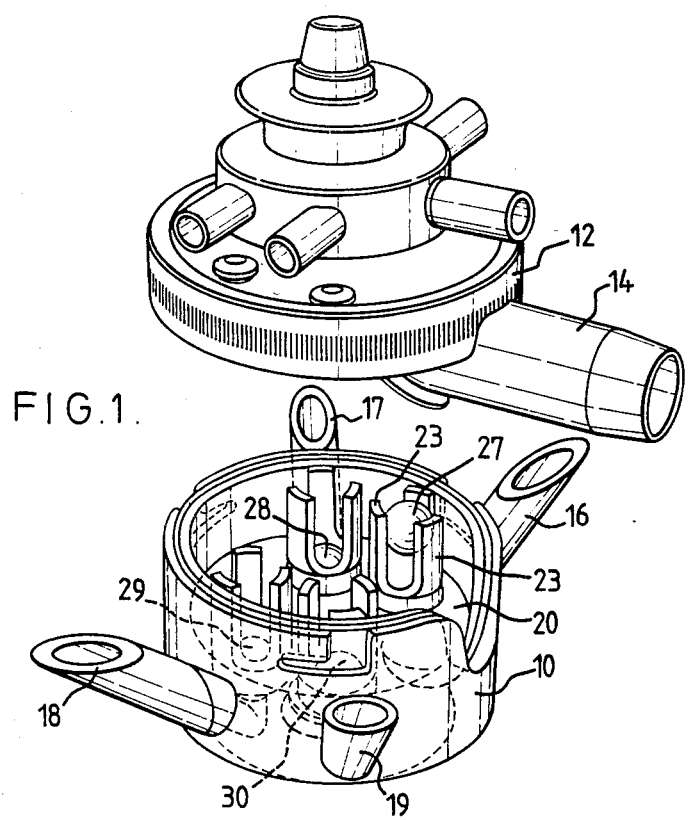
FIG. 1 is an exploded perspective view of a claw-piece according to the invention which is also constructed in accordance with British patent specification No. 2,057,845.

FIG. 1 shows an automatic milking machine claw-piece having a base part 10 and an upper part 12 for sealed attachment to the base part 10. The upper part 12 is a vacuum pulsation distribution block, which need not be further described in connection with the present invention, and also includes the milk output nipple 14.

The base part 10 has four spaced apart milk input nipples 16, 17, 18 and 19. These are downwardly inclined as they enter the body part 10 and then extend upwardly into the interior 20 of the base part 10.

Figure 2:
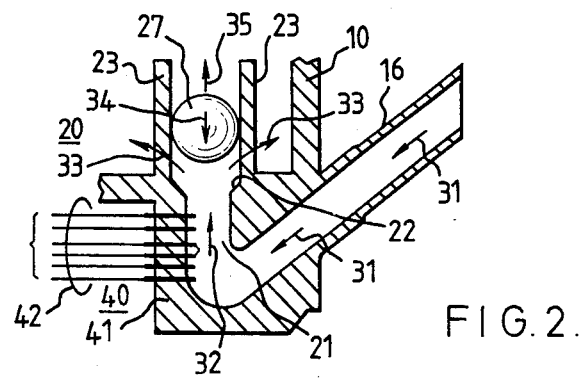
FIG. 2 is a diagrammatic section view of one of the four inlet nipples and associated valve of the claw-piece of FIG. 1.

FIG. 2 shows more clearly the entry passages from the milk input nipples, the construction of all being identical. In FIG. 2, the input nipple 16 is shown downwardly inclined into the body of the base part 10 and then is seen to extend upwardly, as passage 21, past a valve seating 22, between vertical sections 23 of a ball-valve guide and into the interior 20 of the base part 10.

A metal ball closure member 27 is shown in both FIG. 1 and FIG. 2. Corresponding ball closure members 28, 29 and 30, for the corresponding milk input nipples 17, 18 and 19, are also shown in FIG. 1.

As shown in FIG. 2, milk drawn solely from the quarter corresponding to input nipple 16 is drawn into the claw-piece 10 by applied vacuum. In this preferred embodiment of the invention, the method of hydraulic milking is used. That is to say, no air-bleed is permitted during the milking operation up-stream of the valve 22, 27, nor, with respect to the other input nipples 17, 18 and 19, up-stream of the corresponding valves using closure members 28, 29 and 30.

Consequently, a homogeneous column of air-bubble free milk, solely from the one cow's quarter, passes through the input nipple 16, as shown by the arrows 31. This column flows upwardly in the passage 21, as shown by the arrow 32, past the valve seating 22 and into the claw-piece interior 20, as shown by the arrows 33.

In operation, the ball closure member 27 is urged by gravity downwardly, as shown by the arrow 34, onto the valve seating 22, to close the passage 21. This is the rest condition of the valve 22, 27 in the absence of milk flow. Resumed milk flow lifts the ball closure member 27, in the direction of arrow 35, to its open position as shown in FIG. 2.

As also shown in FIG. 2, the body of claw-piece base 10 is cut away at 40 to provide a cylindrical internal cavity, which opens downwardly. This construction provides an inwardly-facing wall of passage 21 having parallel faces over most of its upwards extent. Into this wall are sealed a number of electrodes and sensors. In the present example, the group, shown generally at 41, comprises electrodes for measuring milk conductivity and milk-flow velocity and a sensor for measuring milk temperature.

Alternative or additional electrodes or sensors may be provided as required to monitor a plurality of milk-related values.

In the present example, for monitoring three milk-related values, six electrical leads are brought out, forming a cable shown at 42 in FIG. 2. This cable is identified as cable (a) in FIG. 3.

Figure 3:
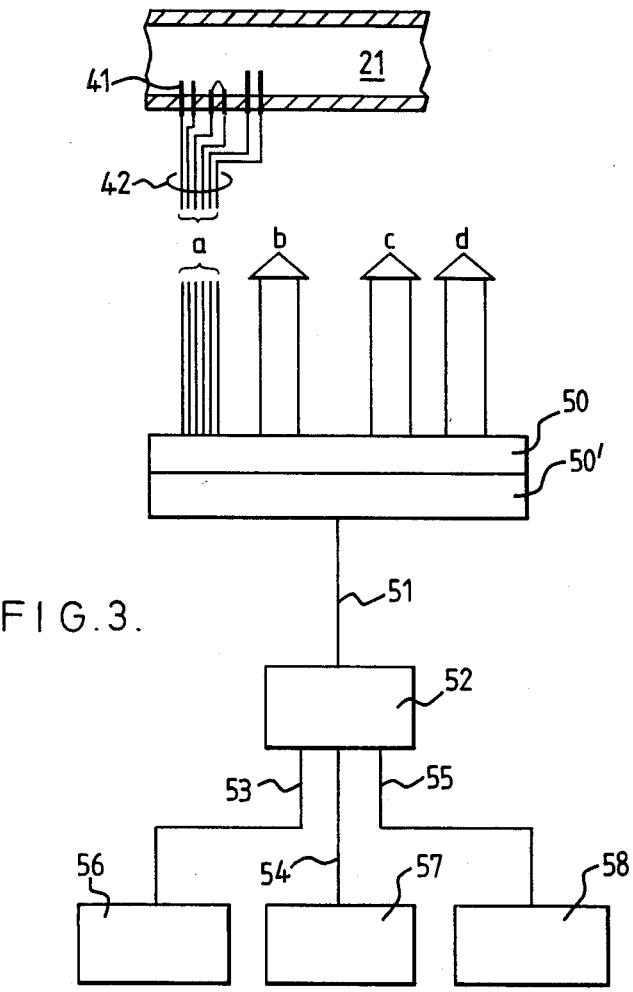
FIG. 3 is a block schematic diagram of the electrical circuitry associated with the claw-piece of FIGS. 1 and 2.

In the block schematic diagram of FIG. 3, the circuit elements described above are shown again with the same reference numerals, the channel 21 being positioned horizontally, for convenience.

The electrical lead group forming cable (a), associated with the milk flow in input nipple 16, and also corresponding cables (b), (c) and (d), associated with the milk flow in input nipples 17, 18 and 19, respectively, are connected as inputs to a circuit selector unit 50.

This unit might comprise mechanical switches but, in the present example, is a solid state switching unit permitting selection of any one to four circuits from the total of twelve circuits connected thereto.

The output of selector unit 50 is fed by line 51 to a data processor 52. The output portion of unit 50, shown at 50', includes such analogue-to-digital interfaces as may be required by the data processor 52 for processing the input signals to unit 50.

The data processor 52 employs a known central processing unit and both computes values in required form and provides output signals of suitable form. Thus, the unit 52 computes milk temperatures from the input signals of (a), (b), (c) and (d), milk volume from the flow-rate signals for any of the four input nipples or a summation value for all four and provides a separate milk-conductivity value for the milk flowing in each input nipple.

These output data values are provided in compatible forms for operating a monitor alarm 56, a data printer 57 and a numerical read-out unit 58, to which the corresponding signals are supplied by way of lines 53, 54 and 55, respectively.

The apparatus of the invention as described above thus permits continuous monitoring during the milking of a single beast. Duplication or multiplication of the apparatus described permits of monitoring the milking of any number of beasts of a dairy herd milked at one time. For each, separate and either simultaneous or sequential monitoring of milk conductivity from each quarter of each beast is provided and an alarm operated if any abnormal value, indicating the presence of mastitis, is detected. Milk temperature from individual beasts is monitored and an alarm operated if an abnormal temperature is detected. Milk volume yield may be computed separately for each quarter or an integrated value computed for individual beasts.

I claim:

1. Automatic milking apparatus comprising a claw-piece, a cluster of four short-milk tubes and associated teat cups for milking the four quarters of a cow, a one-way valve system including a valve means associated with each of the four short-milk tubes for preventing milk from one quarter of the cow from entering the short-milk tube of another quarter of the cow, a group of electrical sensing means, associated with each of the four short-milk tubes, for continuously making electrical measurements of a plurality of values relating to the milk passing through the related short-milk tube and for producing electrical signals in accordance therewith, switch means for selecting electrical sensing means of the four groups for monitoring, a data processing unit for converting electrical signals from said electrical sensing means into meaningful values, and display means for providing a visual display of such values, said claw piece including a base part including four input passages and four input nipples disposed on the upstream side of respective ones of said valve means and respectively connected to said four short-milk tubes, said input nipples comprising a downwardly-inclined portion extending into the claw-piece base and leading to upwardly-inclined passages connected to the respective valve means, a said group of sensing means being located in each of said upwardly-inclined passages, said base of said claw-piece being formed with an internal cavity having an opening at the bottom of the claw-piece and electrical conductors of said electrical sensing means extending into said cavity and away from the claw-piece base by way of said opening.

2. A method of automatic milking of the four quarters of a cow, said method comprising using a claw-piece and cluster of four short-milk tubes and teat cups, excluding air-bleed on the upstream side of the claw-piece during actual milking, passing all milk from each individual quarter through a separate one of four monitoring passages, ensuring by valve means that milk from one quarter does not enter the monitoring passage of another quarter, monitoring by electrical means a plurality of milk-related values for the milk flowing in all four monitoring passages, selecting the values to be monitored and the quarter whose milk is to be monitored at any one time, and providing a visual display of the values so monitored.

3. A method of automatic milking as claimed in claim 2, in which milk from the four quarters of a cow is drawn through respective input nipples, connected to said four short-milk tubes, into the claw-piece through four monitoring passages associated with respective valve means and a group of sensors located on the upstream side of said valve means is used in each one of said monitoring passages.

4. Automatic milking apparatus which comprises a claw-piece and in which air-bleed on the upstream side of the claw-piece is excluded during milking, said apparatus further comprising a cluster of four short-milk tubes and associated teat cups for milking the four quarters of a cow, four monitoring passages within the said claw-piece, each separately carrying the milk from one of the quarters of the cow, a one-way valve means associated with each of the four monitoring passages for preventing milk from one quarter of the cow from entering the monitoring passage of another quarter of the cow, a group of electrical sensing means, each associated with a respective one of the four monitoring passages, for continuously making electrical measurements of a plurality of values relating to the milk passing through the respective monitoring passage and for producing electrical signals in accordance therewith, switching means for selecting sensing means of the four groups of sensing means for monitoring, a data processing means for converting said electrical signals into meaningful values and display means for visual display of such values.

5. Automatic milking apparatus as claimed in claim 4, in which the claw-piece has a base part with four input nipples connected to respective ones of said four short-milk tubes and leading into the four monitoring passages on the upstream side of respective valve means, a group of sensing means being provided in each of the said monitoring passages.

6. Automatic milking apparatus as claimed in claim 5, in which the said input nipples each comprise a downwardly-inclined portion extending into the claw-piece base and leading to upwardly-inclined monitoring passages leading to a respective valve means, each said group of sensing means being located in a respective said upwardly-inclined monitoring passage.

7. Automatic milking apparatus as claimed in claim 6, in which the base of the claw-piece is formed with an internal cavity having an opening at the bottom of the claw-piece and electrical conductors of the said groups of sensing means extend into the said cavity and away from the claw-piece base by way of the said opening.

* * * * *